(12) United States Patent
Itoh et al.

(10) Patent No.: US 7,544,515 B2
(45) Date of Patent: Jun. 9, 2009

(54) METHOD OF QUANTIFYING SMALL-SIZED LOW DENSITY LIPOPROTEIN

(75) Inventors: Yasuki Itoh, Niigata (JP); Tsutomi Hirano, Tokyo (JP)

(73) Assignee: Denka Seiken Co., Ltd., Tokyo (JP)

( * ) Notice: Subject to any disclaimer, the term of this patent is extended or adjusted under 35 U.S.C. 154(b) by 126 days.

(21) Appl. No.: 10/537,766

(22) PCT Filed: Dec. 5, 2003

(86) PCT No.: PCT/JP03/15633

§ 371 (c)(1),
(2), (4) Date: Jun. 6, 2005

(87) PCT Pub. No.: WO2004/053500

PCT Pub. Date: Jun. 24, 2004

(65) Prior Publication Data

US 2006/0154374 A1    Jul. 13, 2006

(30) Foreign Application Priority Data

Dec. 6, 2002    (JP)    ............................. 2002-355119

(51) Int. Cl.
G01N 33/92    (2006.01)
(52) U.S. Cl. ..................... 436/71; 436/79; 436/174; 436/175; 436/177
(58) Field of Classification Search .................. 436/13, 436/63, 71, 174, 175, 177; 422/61, 101
See application file for complete search history.

(56) References Cited

U.S. PATENT DOCUMENTS

| 4,215,993 | A | * | 8/1980 | Sanders | ........................ | 436/71 |
| 4,521,519 | A | * | 6/1985 | Draeger et al. | ................ | 436/17 |
| 4,923,439 | A | * | 5/1990 | Seidel et al. | ................ | 604/5.03 |
| 5,057,226 | A | * | 10/1991 | Antwiler | ...................... | 210/641 |
| 5,691,159 | A | * | 11/1997 | Miyauchi et al. | .............. | 435/11 |
| 5,736,406 | A | * | 4/1998 | Miyauchi et al. | .............. | 436/71 |
| 5,888,755 | A | * | 3/1999 | Miyauchi et al. | .............. | 435/11 |
| 6,642,055 | B1 | * | 11/2003 | Arbogast | ..................... | 436/88 |
| 6,794,157 | B1 | * | 9/2004 | Sugiuchi | ...................... | 435/11 |
| 6,811,994 | B1 | * | 11/2004 | Miyauchi et al. | .............. | 435/18 |

FOREIGN PATENT DOCUMENTS

| EP | 1 114 870 A1 | 7/2001 |
| JP | 7-294532 A | 11/1995 |
| JP | 2000-356641 A | 12/2000 |
| JP | 2003-28882 A | 1/2003 |

(Continued)

OTHER PUBLICATIONS

Hirano et al. Journal of Lipid Research, vol. 44, Aug. 1, 2003, pp. 2193-2201.*

(Continued)

*Primary Examiner*—Maureen M Wallenhorst
(74) *Attorney, Agent, or Firm*—Stephen A. Bent; Foley & Lardner LLP

(57) ABSTRACT

A fast and simple method for fractional measurement of a small particle LDL entails separating the small particle LDL and HDL from other lipoproteins, and then measuring cholesterol, triglycerides, or proteins in the separated small particle LDL.

20 Claims, 10 Drawing Sheets

FOREIGN PATENT DOCUMENTS

WO 00/17388 * 3/2000

OTHER PUBLICATIONS

English language translation of JP 07294532, Nov. 10, 1995.*
International Search Report of PCT/JP03/15633.
Atherosclerosis, vol. 106, (1994), pp. 241-253.
Martin Petersen et al., "Effect of Fish Oil Versus Corn Oil Supplementation on LDL and HDL Subclasses in Type 2 Diabetic Patients", Diabetes Care, vol. 25, No. 10, Oct. 2002, pp. 1704-1708.

Mark R. McCall et al., "Dissociable and nondissociable forms of platelet-activating factor acetylhydrolase in human plasma LDL: implications for LDL oxidative susceptibility", Biochimica et Biophysica Acta 1437 (1999) pp. 23-76.

G. Russell Warnick et al., "A comprehensive evaluation of the heparin-manganese precipitation procedure for estimating high density lipoprotein cholesterol", Journal of Lipid Research, vol. 19, 1978, pp. 65-76.

* cited by examiner

Lane No. 1  Sample rich in LDL other than small particle LDL, before the reaction Lane No. 2  Sample rich in small particle LDL before the reaction Lane No. 3  Sample rich in LDL other than small particle LDL, after the reaction Lane No. 4  Sample rich in small particle LDL, after the reaction.

METHOD OF QUANTIFYING SMALL-SIZED LOW DENSITY LIPOPROTEIN

TECHNICAL FIELD

The present invention relates to a method for fractional quantitative measurements of small particle low density lipoproteins which is important for clinical diagnosis of arteriosclerosis.

BACKGROUND ART

Low density lipoproteins (LDLs) play a major role in cholesterol transport in the blood and is a risk factor for arteriosclerosis. It is known that a small particle low density lipoprotein (hereinafter "small particle LDL"), which is especially smaller in particle size among LDLs and higher in density than standard LDL, is associated with a several fold increase in risk for arteriosclerosis as compared to normal LDL. Increase of small particle LDL is one of the major risk factors for arteriosclerosis. It is clinically very important to have a fractional measurement for small particle LDL.

The conventional methods for measuring small particle LDL use ultracentrifugation, electrophoresis, high speed liquid chromatography and the like. The ultracentrifugation method isolates small particle LDL by using differences in the density, and the quantities of cholesterol and protein therein are measured. Small particle LDL is fractionated in densities between 1.040 and 1.063 (Atherosclerosis, 48 p. 33-49, 1993: Atherosclerosis, 106, p. 241-253, 1994, etc.). However, this method requires expensive facilities, and it is time consuming to make measurements. The electrophoresis method measures the mobility and the particle diameter of a LDL using a polyacrylamide gel. The particle size of a small particle LDL is below 25.5 nm (JAMA, 260, p. 1917-21, 1988, etc.), and the relative mobility of LDLs (moving distance from VLDL to LDL divided by the moving distance from VLDL to HDL) is not less than 0.4 (Domyakukoka (arteriosclerosis), 25, p. 67-70, 1997). However, these methods are for measuring the degree of a small LDL particle in LDLs, and they are not used to obtain a quantitative measurement. Also, the number of samples that can be tested at one time is limited, and it takes a long time to make measurements. Recently, a method for measuring lipoprotein was invented. In this method, after electrophoresis, an agarose gel is stained for a lipid, and the staining pattern is analyzed using a computer, and a quantitative measurement of lipoprotein is obtained (Japanese Patent Publication Laid Open No. 2000-356641). This is a method for analyzing denatured LDL such as oxidized LDL, acetylated LDL, glycosylated LDL, MDA-LDL and the like. Small particle LDLs can not be measured accurately by this method. Since the analysis requires very expensive equipment, this is not suitable for general use.

Conventionally, in the measurement of a HDL, it is known that a combination of a polyanion with a divalent cation can be used as a separation agent to isolate the HDL by coagulating lipoproteins other than HDL. For example, methods using dextran sulfate-$Mg^{2+}$ (Clin. Chem., 28, p. 1379-88, 1982, and the like), heparin-$Mn^{2+}$ (J Lipid Res. 19, p. 65-76, 1978, and the like), heparin-$Ca^{2+}$ (Arch. Biochem. Biophys., 170, p. 334-40, 1975, and the like)and phosphotungstic acid-$Mg^{2+}$ (Clin. Chem., 23, p. 882-84, 1977, and the like)and the like are known. Further, a method has been reported for calculating the fractions of LDL and VLDL by stepwise precipitations of lipoproteins using several separation agents (Japanese Patent Publication Laid Open No. 7-294532, Rinsho-Byori, Special Edition 21, 82, 1975, and the like). Still further, a method for separating HDL using polyethylene glycol has also been reported (Ann. Clin. Biochem. 18 p. 177-81, 1981).

Furthermore, there have been conventional methods such as a method in which by stepwise precipitation of the lipoproteins using a plurality of separation agents, each lipoprotein is measured based on differences in their turbidity (Rinsho-Byori, Special Edition 21, 82, 1975, and the like), and a method in which a small particle LDL is suspended or dissolved according to differences in ionic strength and the small particle LDL is measured by differences in absorbency (Japanese Patent Publication Laid Open No. 2003-28882). However, because light absorbency is measured, specificity and accuracy have been insufficient.

Patent document 1 Japanese Patent Publication Laid Open No. 2000-356641
Patent document 2 Japanese Patent Publication Laid Open No. 7-294532
Patent document 3 Japanese Patent Publication Laid Open No. 2003-28882
Non-patent document 1 Atherosclerosis, 48 p. 33-49, 1993
Non-patent document 2 Atherosclerosis, 106, p. 241-253, 1994
Non-patent document 3 JAMA, 260, p. 1917-21, 1988
Non-patent document 4 Domyakukoka, 25, p. 67-70, 1997
Non-patent document 5 Clin. Chem., 28, p. 1379-88, 1982
Non-patent document 6 J Lipid Res. 19, p. 65-76, 1978
Non-patent document 7 Arch. Biochem. Biophys., 170, p. 334-40, 1975
Non-patent document 8 Clin. Chem., 23, p. 882-84, 1977
Non-patent document 9 Rinsho-Byori, Special Edition 21, 82, 1975
Non-patent document 10 Ann. Clin. Biochem. 18 p. 177-81, 1981

DISCLOSURE OF THE INVENTION

The object of the present invention is to provide a fast and simple method for fractional measurement of a small particle LDL.

As described above, the use of separation agents such as polyanions, divalent cations and the like for coagulating lipoproteins other than HDLs in a lipoprotein mixture has been reported. Major fractions in the lipoprotein mixture such as VLDL, LDL and HDL may be separated by the separation agents due to differences in their physical properties. However, no attempt has been made to separate LDL into subfractions by a similar method.

The present inventors, having extensively investigated methods for separating a small particle LDL, discovered that a small particle LDL may be separated from other LDLs by treating the test sample with a polyanion and a divalent cation at appropriate concentrations. Better separation of a small particle LDL is achieved by further adding a monovalent cation which acts as an ionic strength adjuster. Further, a similar effect was obtained by using PEG in place of the polyanion, divalent cation and monovalent cation.

The present inventors have investigated in detail the concentrations of the polyanion, divalent cation and monovalent cation when they are used in combination and also the concentration of PEG when PEG is used. By establishing a range of concentrations to be used, they discovered the conditions under which a small particle LDL may be separated from a LDL particle mixture by coagulating the LDL other than small particle LDLs. By this reaction, the LDL other than small particle LDLs forms a coagula, which will be eliminated from the reaction mixture by centrifugation or filtration. By applying a reagent for measuring LDL cholesterol, a reagent for measuring triglycerides in a LDL, or anti-human apoprotein B antibody to the reaction mixture after coagula removal, the cholesterol, triglycerides or protein in the small particle LDL can be quantitatively measured, and thus the present invention is completed.

Compared to above described method for measuring a small particle LDL based on differences in absorbency after suspending or dissolving the small particle LDL utilizing differences in ionic strength (Japanese Patent Publication Laid Open No. 2003-28882), the present invention is superior in specificity and accuracy because cholesterol, triglycerides and protein are measured in small particle LDL after separation.

The present invention provides the following methods and kits:

(1) A method for quantifying a small particle low density lipoprotein in a test sample, comprising a first step for separating the small particle low density lipoprotein from other low density lipoproteins, and a second step for measuring cholesterol, triglycerides or proteins in the separated small particle low density lipoprotein.

(2) A method according to (1) wherein a polyanion and a divalent cation are used for separating the small particle low density lipoprotein from other low density lipoproteins in the first step.

(3) A method according to (1) or (2) wherein a monovalent cation is further used for separating the small particle low density lipoprotein from other low density lipoproteins in the first step.

(4) A method according to (2) or (3) wherein the polyanion used in the first step is selected from the group consisting of a group consisting of heparin, phosphotungstic acid and dextran sulfate.

(5) A method according to any one of (2) to (4) wherein the divalent cation used in the first step is selected from the group consisting of a group consisting of $Mn^{2+}$, $Mg^{2+}$ and $Ca^{2+}$.

(6) A method according to (3) or (5) wherein the monovalent cation used in the first step is selected from the group consisting of a group consisting of $Na^+$, $K^+$ and $Li^+$.

(7) A method according to any one of (4) to (6) wherein, when the polyanion is added to the test sample, the final concentration of the polyanion is 10-250 U/mL for heparin, 0.02-1.25% for dextran sulfate and 0.02-1.25% for phosphotungstic acid.

(8) A method according to any one of (5) to (7) wherein, when the divalent cation is added to the test sample, the final concentration of the divalent cation is 2.5-35 mmol/L for $Mn^{2+}$, 2.5-125 mmol/L for $Mg^{2+}$ and 1-75 mmol/L for $Ca^{2+}$.

(9) A method according to any one of (6) to (8) wherein, when the monovalent cation is added to the test sample, the final concentration of the monovalent cation is 0-50 mmol/L.

(10) A method according to (1) wherein PEG is used to separate the small particle low density lipoprotein from other low density lipoproteins in the first step.

(11) A method according to (10) wherein the final concentration of PEG is 2-5% when PEG is added to the test sample.

(12) A method according to any one of (1) to (11) wherein the measurement of cholesterol in the second step is carried out by using a reagent which is used for quantitatively measuring cholesterol in a low density lipoprotein and which does not require fractionation.

(13) A method according to any one of (1) to (11) wherein the measurement of triglycerides in the second step is carried out by using a reagent which is used for quantitatively measuring triglycerides in low density lipoprotein and which does not require fractionation.

(14) A method according to any one of (1) to (11) wherein the measurement of protein in the second step is carried out by using anti-human apoprotein B antibody.

(15) A method for separating a small particle low density lipoprotein from a test sample comprising a step in which the low density lipoprotein other than small particle low density lipoproteins is precipitated by adding a polyanion and a divalent cation to the test sample.

(16) A method according to (15) comprising a step in which the low density lipoprotein other than small particle low density lipoproteins is precipitated by also adding a monovalent cation to the test sample.

(17) A method for separating a small particle low density lipoprotein according to (15) or (16), wherein the polyanion is selected from the group consisting of a group consisting of heparin, phosphotungstic acid and dextran sulfate.

(18) A method for separating a small particle low density lipoprotein according to any one of (15) to (17), wherein the divalent cation is selected from the group consisting of a group consisting of $Mn^{2+}$, $Mg^{2+}$ and $Ca^{2+}$.

(19) A method for separating a small particle low density lipoprotein according to any one of (15) to (18) wherein the monovalent cation is selected from the group consisting of a group consisting of $Na^+$, $K^+$ and $Li^+$.

(20) A method for separating a small particle low density lipoprotein according to any one of (17) to (19), wherein, when the polyanion is added to the test sample, the final concentration of the polyanion is 10-250 U/mL for heparin, 0.02-1.25% for dextran sulfate and 0.02-1.25% for phosphotungstic acid.

(21) A method for separating a small particle low density lipoprotein according to any one of (18) to (20), wherein, when the divalent cation is added to the test sample, the final concentration of the divalent cation is 2.5-35 mmol/L for $Mn^{2+}$, 2.5-125 mmol/L for $Mg^{2+}$ and 1-75 mmol/L for $Ca^{2+}$.

(22) A method for separating a small particle low density lipoprotein according to any one of (19) to (21), wherein, when the monovalent cation is added to the test sample, the final concentration of the monovalent cation is 0-50 mmol/L.

(23) A method for separating a small particle low density lipoprotein from a test sample comprising a step in which PEG is added to the test sample to precipitate the low density lipoprotein other than small particle low density lipoproteins.

(24) A method for separating a small particle low density lipoprotein according to (23) wherein the final concentration of PEG is 2-5% when PEG is added to the test sample.

(25) A kit for measuring a small particle low density lipoprotein comprising: a separation agent that includes a polyanion and a divalent cation; and a reagent for measuring the low density lipoprotein, wherein the kit measures cholesterol, triglycerides or proteins in the small particle low density lipoprotein.

(26) A kit for measuring a small particle low density lipoprotein according to (25), wherein the separation agent further includes a monovalent cation.

(27) A kit for measuring a small particle low density lipoprotein comprising: a separation agent that includes PEG; and a reagent for measuring the low density lipoprotein, wherein the kit measures cholesterol, triglycerides or proteins in the small particle low density lipoprotein.

(28) A kit according to (25) or (26) wherein the polyanion is selected from the group consisting of a group consisting of heparin, phosphotungstic acid and dextran sulfate.

(29) A kit according to (26) or (28) wherein the divalent cation is selected from the group consisting of a group consisting of $Mn^{2+}$, $Mg^{2+}$ and $Ca^{2+}$ and the monovalent cation is selected from the group consisting of a group consisting of $Na^+$, $K^+$ and $Li^+$.

This description hereby incorporates the entire content of the description and/or the drawings of the Japanese Patent Application No. 2002-35519 that is the basis of the priority claim of this application.

BEST MODE FOR CARRYING OUT THE INVENTION

Figure 1:
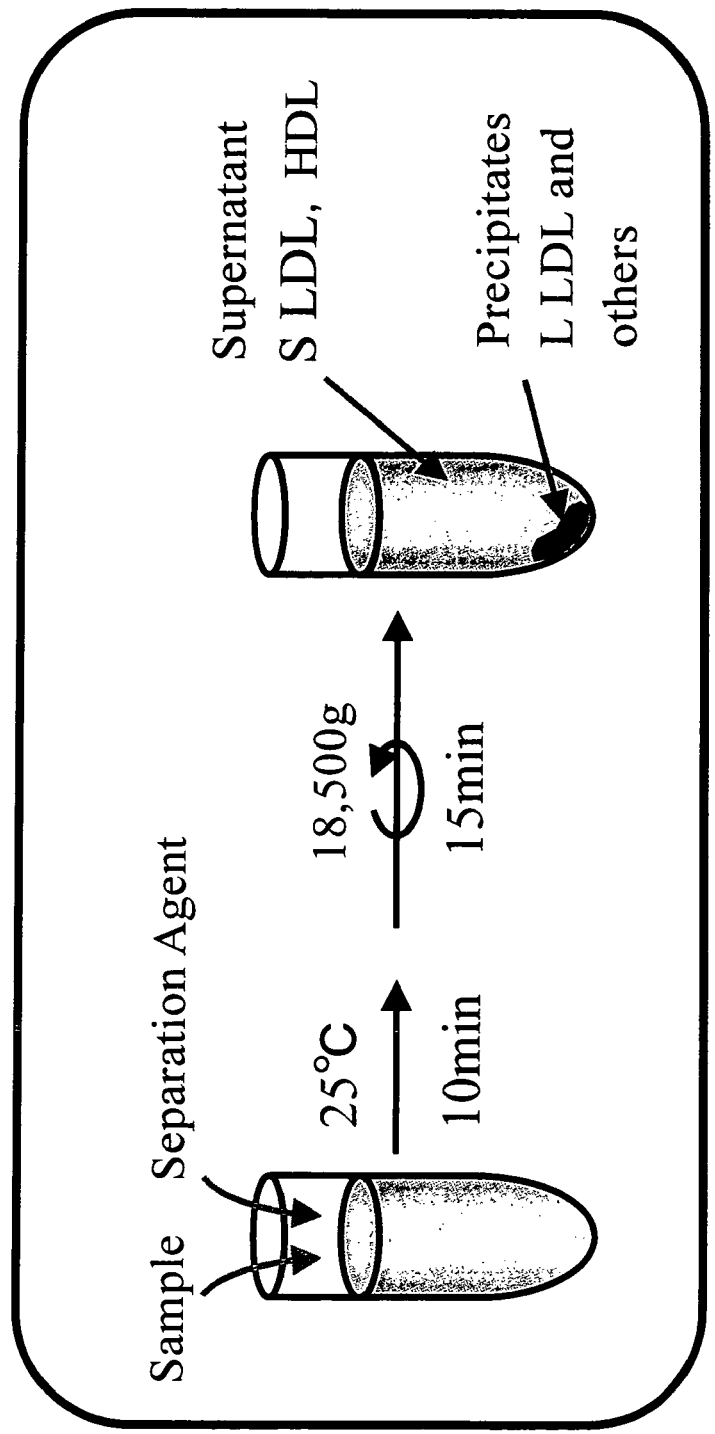
FIG. 1 illustrates the first step of the method of the present invention.

The present invention will be explained in detail as follows.

The method of the present invention comprises a first step and a second step. In the first step, a test sample is mixed with a separation fluid containing a polyanion and a divalent cation or with another separation fluid containing a polyanion, a divalent cation and a monovalent cation or with PEG. After reacting the mixture for a predetermined time, VLDLs and LDLs other than a small dense particle is coagulated and removed by centrifugation or filtration. In the second step, cholesterol, triglyceride and protein in the small particle LDL are measured. In the first step, the HDLs as well as the small particle LDL remain in the solution after the above mentioned lipoprotein is removed. However, fractional measurements may be performed on the small particle LDL component only, by using a LDL cholesterol measuring reagent or a triglyceride measuring reagent for LDLs, or by applying an anti-human apoprotein B antibody.

As described above, a lipoprotein can be fractionated roughly into VLDLs, LDLs and HDLs, and LDL is sub-fractionated into a small particle LDL and other sub-fractions. A small particle LDL is also called SLDL (small LDL), small dense LDL or dense LDL, and LDL other than small particle LDL is sometimes called LLDL (large LDL) or Light LDL. These fractions and sub-fractions may be distinguished based on particle size or specific gravity. The particle size in diameter is, 30 nm-80 nm (30 nm-75 nm) for VLDL, 22 nm-28 nm (19 nm-30 nm) for LDL and 7 nm-10 nm for HDL, although they may vary depending on the researchers. The density is below 1.006 for VLDL, 1.019-1.063 for LDL and 1.063-1.21 for HDL. The diameter of LDL particles can be measured by gradient gel electrophoresis (GGE) (JAMA, 260, p. 1917-21, 1988) or NMR(HANDBOOK OF LIPOPROTEIN TESTING $2^{nd}$ Edition, Edited by Nader Rifai et al. p. 609-623, AACC PRESS:The Fats of Life Summer 2002, LVDD 15 YEAR ANNIVERSARY ISSUE, Volume AVI No. 3, p. 15-16), and the specific gravity may be determined based on analyses by ultracentrifugation (Atherosclerosis, 106, p. 241-253, 1994: Atherosclerosis, 83, p. 59, 1990).

The small particle LDL to be measured in the present invention is, in general, a sub-fraction of the LDL fraction, the diameter of which is about 22.0 nm to approximately 25.5 nm, and the specific gravity of which is 1.040-1.063. The reason why LDL is sub-fractionated according to the particle size is that a small LDL among LDLs needs to be fractionally measured because LDL with a small particle diameter causes more arteriosclerosis and is higher in malignancy than other LDLs. Since the distributions of diameter and specific gravity of a LDL are continuous, it is not possible to determine the value of specific gravity above which the malignancy is clearly higher. Thus the specific gravity value of 1.040-1.063 described above is not an established characteristic of a small particle LDL, but it is the median point of the specific gravity range of 1.019-1.063 which is widely used and established as the specific gravity of LDL. For example, in a different report, small particle LDL is fractionated in the range of 1.044-1.069 (Atherosclerosis:106 241-253 1994). There are some differences among researchers on how to set the range of the specific gravity of a small particle LDL, but with any of the ranges chosen, the presence of a small particle LDL is associated with clinical malignancy.

In the present invention, a small particle LDL is defined as a LDL with a high specific gravity among LDLs and with a higher association with arteriosclerosis clinically than other LDLs. Preferably, the small particle LDL has a specific gravity range greater than the median point within the range of specific gravity for LDLs. More preferably, the small particle LDL is a LDL with the specific gravity in the range of 1.040-1.063.

The test sample used in the method of the present invention is serum or plasma, and preferably serum. In the first step, an appropriate volume of sample is mixed with a polyanion and a divalent cation or a polyanion, a divalent cation and a monovalent cation, so that the final concentrations of the polyanion, divalent cation and monovalent cation are predetermined values. A small particle LDL may be separated from other LDLs in the presence of a polyanion and a divalent cation, but better separation of the fraction containing small particle LDL and HDL may be achieved by the further presence of a monovalent cation which acts as an ionic strength adjuster. In this step, a separation solution containing predetermined concentrations of polyanion and divalent cation, or a separation solution containing predetermined concentrations of polyanion, divalent cation and monovalent cation may be prepared and added to the test sample. It is also possible to prepare the solutions of the polyanion, divalent cation and monovalent cation separately at the predetermined concentrations, and to add these solutions separately to the test sample. The order of addition of these individual solutions to the test sample is not limited. The solvent used to prepare the solution containing the polyanion and divalent cation or the solution containing polyanion, divalent cation and monovalent cation may be purified water, physiological saline and various buffers. The pH of the separation solution is preferably 3-8.

The polyanion used in the first step is preferably heparin, phosphotungstic acid or dexrtran sulfate. After adding the polyanion and divalent cation, or the polyanion, divalent cation and monovalent cation to the test sample, the preferred final concentration of the polyanion is 10-250 U/mL for heparin, 0.02-1.25% for phosphotungstic and 0.02-1.25% for dextran sulfate.

The divalent metal ion used in the first step may be $Mn^{2+}$, $Mg^{2+}$, $Ca^{2+}$ or $Co^{2+}$, and is preferably $Mn^{2+}$, $Mg^{2+}$, $Ca^{2+}$. After adding the polyanion and divalent cation to the test sample, the preferred final concentration of the divalent cation is: 7.5-35 mmol/L for $Mn^{2+}$, 40-125 mmol/L for $Mg^{2+}$ and 50-75 mmol/L for $Ca^{2+}$ if heparin is used as the polyanion; 2.5-7.5 mmol/L for $Mn^{2+}$, 2.5-50 mmol/L for $Mg^{2+}$ and 1-30 mmol/L for $Ca^{2+}$ if phosphotungstic acid is used as the polyanion; 2.5-10 mmol/L for $Mn^{2+}$, 7.5-30 mmol/L for $Mg^{2+}$ and 5-20 mmol/L for $Ca^{2+}$ if dextran sulfate is used as the polyanion.

Further, when a monovalent cation is used in the first step, a monovalent metal ion such as $Na^+$, $K^+$ and $Li^+$ is preferably used. The preferred final concentration of the monovalent cation is 0-50 mmol/L.

For example, 100 µl of the test sample is mixed with 100 µl of a separation agent containing a polyanion and a divalent cation or a separation agent containing a polyanion, a divalent cation and a monovalent cation. The concentrations of the polyanion, divalent cation and monovalent cation in the separation agents may be adjusted so that the concentrations of the polyanion, divalent cation and monovalent cation in the mixture of the test sample and the separation agent are the final concentrations described above. The concentration of the polyanion in the separation agent is preferably 20-500 U/mL for heparin, 0.04-2.5% for phosphotungstic acid and 0.04-2.5% for dextran sulfate. The preferred final concentration of the divalent cation in the separation agent is: 15-70 mmol/L for $Mn^{2+}$, 80-250 mmol/L for $Mg^{2+}$ and 100-150 mmol/L for $Ca^{2+}$ if heparin is used as the polyanion; 5-15 mmol/L for $Mn^{2+}$, 5-100 mmol/L for $Mg^{2+}$ and 2-60 mmol/L for $Ca^{2+}$ if phosphotungstic acid is used as the polyanion; 5-20 mmol/L for $Mn^{2+}$, 15-60 mmol/L for $Mg^{2+}$ and 10-40 mmol/L for $Ca^{2+}$ if dextran sulfate is used as the polyanion. The preferred concentration of the monovalent cation is 0-100 mmol/L.

After adding the polyanion and divalent cation or the polyanion, divalent cation and monovalent cation to the test sample, the reaction mixture is stirred to cause the reaction of the first step.

It is preferable to carry out the reaction of the first step at a temperature of 2° C.-45° C., and more preferably at 20° C.-37° C.

It is preferable to carry out the reaction of the first step for 1 min to 30 mins, and more preferably for 5 mins to 15 mins.

Further, the optimum concentrations of the polyanion, divalent cation and monovalent cation in the first step may vary depending on the combination of the type of polyanion, divalent cation and monovalent cation used and also depending on the pH, ionic strength and the like of the test sample. Thus, the reaction of the first step of the present invention does not necessarily yield the same range for the specific gravity all the time. In particular, small particle LDL with the specific gravity in the range 1.040-1.063 as described above is not necessarily obtained. However, if the reaction of the first step is carried out with the concentrations described above, LDL with an almost equal range of specific gravity may be obtained, and this LDL is included in the LDL defined as above. Furthermore, the above description is based on the idea that the specific gravity of small particle LDL has a fixed range of 1.040-1.063, and even if the specific gravity of LDL obtained in the first step of the present invention is slightly out of this range, the difference is not large. The fraction still contains a relatively small particle LDL among the whole LDLs, and thus the amount of the small particle LDL obtained in the first step of the present invention reflects the risk of arteriosclerosis of a patient from whom the test sample is obtained.

Separation of the fraction containing the small particle LDL and HDL in the first step may be carried out by adding polyethylene glycol (PEG) to the test sample in place of the polyanion and divalent cation or the polyanion, divalent cation and monovalent cation. The molecular weight of PEG used here is preferably 4,000-20,000, and the final concentration of PEG is preferably 4-10%.

After completing the reaction of the first step, the fraction containing the small particle LDL and HDL may be obtained by centrifuging and collecting the supernatant. The conditions for centrifugation are at 9,000 g-36,000 g for 1-30 mins.

After completing the reaction of the first step, the fraction containing small particle LDL and HDL may also be obtained as the pass through fraction by filtering the reaction mixture. The filter may be a pressure filtration type or a centrifugal filtration type. The pore size of the filter used is 0.10-0.80 micrometers, and for example, commercially available Milex, Ultrafree (MILLIPORE Co.), Minisart (Sartorius Co.), DISMIC (ADVANTEC Co.), HT Tuffryn Acrodisc Syringe Filter (PALL Gelman Laboratory Co.) and the like may be used.

By measuring only the LDL in the fraction containing small particle LDL and HDL obtained in the first step, the small particle LDL in the test sample may be measured.

The LDL measurement may be carried out by measuring cholesterol in LDL, triglycerides in LDL or apoB protein in LDL.

For the second step, several methods for measurement of LDL cholesterol which does not require a fractionation procedure have been reported (Japanese Patent Publication Laid Open No. 11-318496, 2002-202314, 10-080300, 09-313200, 11-155595, Japanese Patent Publication No. 3256241, and the like), and these methods may be preferably used.

For example, LDL in the fraction obtained in the first step containing small particle LDL and HDL may be measured according to the method described in Japanese Patent Publication Laid Open No. 11-318496 as follows. The test sample, which is the fraction obtained in the first step containing the small particle LDL and HDL, is treated with cholesterol esterase and cholesterol oxidase in the presence of a surface active agent which acts on lipoproteins other than LDL. Hydrogen peroxide generated in the reaction is removed. These reactions eliminate lipoproteins other than LDL from the test sample (step A), and then the residual LDL in the test sample may be measured (step B). The surface active agent that acts on lipoproteins other than LDL includes polyalkylene oxide derivatives with a HLB value of 13 or above and 15 or below. For example, polyoxyethylene lauryl ether, polyoxyetylene cetyl ether, polyoxyethylene oleyl ether, polyoxyethylene higher alcohol ether, polyoxyetylene octylphenyl ether, polyoxyetylene nonylphenyl ether and the like are included which are compounds with HLB values of 13 or above and 15 or below. The preferred concentration of the above mentioned surface active agent used in step A is about 0.1-10 g/L and more preferably, about 0.5-5.0 g/L. The method for removing hydrogen peroxide includes a method using catalase to degrade the hydrogen peroxide to water and oxygen, and a method using peroxidase by which a phenolic or aniline hydrogen donor is reacted with hydrogen peroxide and is converted to colorless quinone, but it is not limited to these.

The preferred concentration of cholesterol esterase in the reaction mixture of step A is about 0.2-1.0 U/mL, and the cholesterol esterase produced by bacteria of the genus Pseudomonas is effective. The preferred concentration of cholesterol oxidase is about 0.1-0.7 U/mL, and cholesterol oxidase produced by bacteria or yeast is preferably used. Further, the preferred concentration of catalase is about 40-100 U/mL. Still further, the preferred concentration of peroxidase, when it is used to convert hydrogen peroxide to colorless quinone, is 0.4-1.0 U/mL, and the preferred concentration of the phenolic or aniline hydrogen donor is 0.4-0.8 mmol/L. In step B, the residual cholesterol in the test sample is measured. For example, the assay may be carried out by adding a surface active agent which acts at least on LDL and by measuring the hydrogen peroxide generated by the action of cholesterol esterase and cholesterol oxidase. The surface active agent which acts on LDL includes polyalkylene oxide derivatives with a HLB value of 11 or above and 13 or below. For example, polyoxyethylene lauryl ether, polyoxyetylene cetyl ether, polyoxyethylene oleyl ether, polyoxyethylene higher alcohol ether, polyoxyetylene octylphenyl ether, polyoxyetylene nonylphenyl ether and the like are included which are compounds with a HLB value of 11 or above and 13 or below. The preferred reaction conditions for step B is similar to the preferred conditions for step A.

Kits for measuring LDL are commercially available, and LDL may be measured using these commercial kits. For example, the commercially available LDL-EX(N) (DENKA SEIKEN Co.) may be used.

For the second step, several methods are available for measuring triglycerides in the LDL which do not require fractionation (WO Publication No. 00/43537 and the like), and these methods may be used appropriately.

For the second step, several methods are available for applying anti-human apoB antibody (Japanese Patent Publication No. 2638137, Japanese Patent Publication Laid Open No. 02-64458 and the like), and these methods may be used appropriately.

The present invention includes a kit containing reagents for the first step where the fraction containing small particle LDL is separated and reagents for measuring the separated small particle LDL. The kit may contain, for example, the above mentioned reagent kit for measuring a LDL, and a polyanion and divalent cation (or the separating agent containing the polyanion and divalent cation) and the like. Furthermore, the kit may contain tubes for centrifugation and separation filters for a small particle LDL. The kit may also contain a monovalent cation in addition to the polyanion and divalent cation. In this case, the kit may contain a separation agent which includes the polyanion, divalent cation and monovalent cation. Still further, the kit may contain polyethylene glycol in place of the polyanion and divalent cation.

The present invention will be explained particularly based on the embodiments as follows. However, the present invention is not limited to the embodiments described below.

EXAMPLE 1

Figure 2:
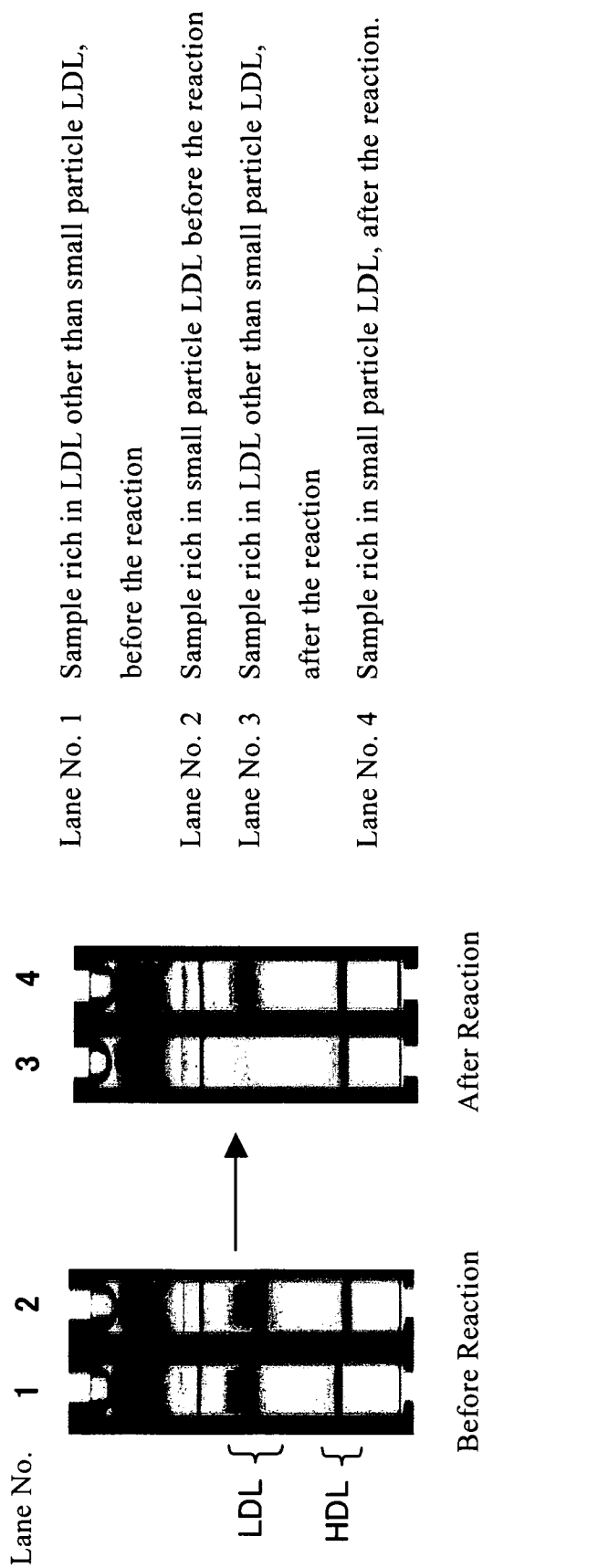
FIG. 2 illustrates the effect of the first step of the present invention in Example 1.

Efficiency of the first step was studied on samples which were confirmed to contain mainly a small particle LDL by electrophoresis, and other samples which were rich in LDLs other than a small particle LDL. Fifty μl of serum was mixed with 50 μl of a separation solution containing 60 U/mL of sodium heparin and 40 mmol/L of $MnCl_2$, and the reaction was allowed to continue at 25° C. for 15 mins. Then the mixture was centrifuged at 18,500 g for 15 mins, the supernatant was recovered, and the reactivity was compared using a commercially available disc type polyacrylamide gel lipophore. The separation solution and the sera before the reaction were electrophoresed after dilution with an equal volume of physiological saline. FIG. 1 shows the method in the step 1 of the present invention and FIG. 2 shows the results. FIG. 2 demonstrates that only normal LDL is selectively removed. In FIG. 2, the lane No. 1 demonstrates the result of electrophoresis of the sample rich in LDL other than small particle LDL before the reaction; the lane No. 2 demonstrates the result of electrophoresis of the sample rich in small particle LDL before the reaction; the lane No. 3 demonstrates the result of electrophoresis of the sample rich in LDL other than small particle LDL after the reaction; and the lane No. 4 demonstrated the result of electrophoresis of the sample rich in small particle LDL after the reaction.

EXAMPLE 2

Figure 3:
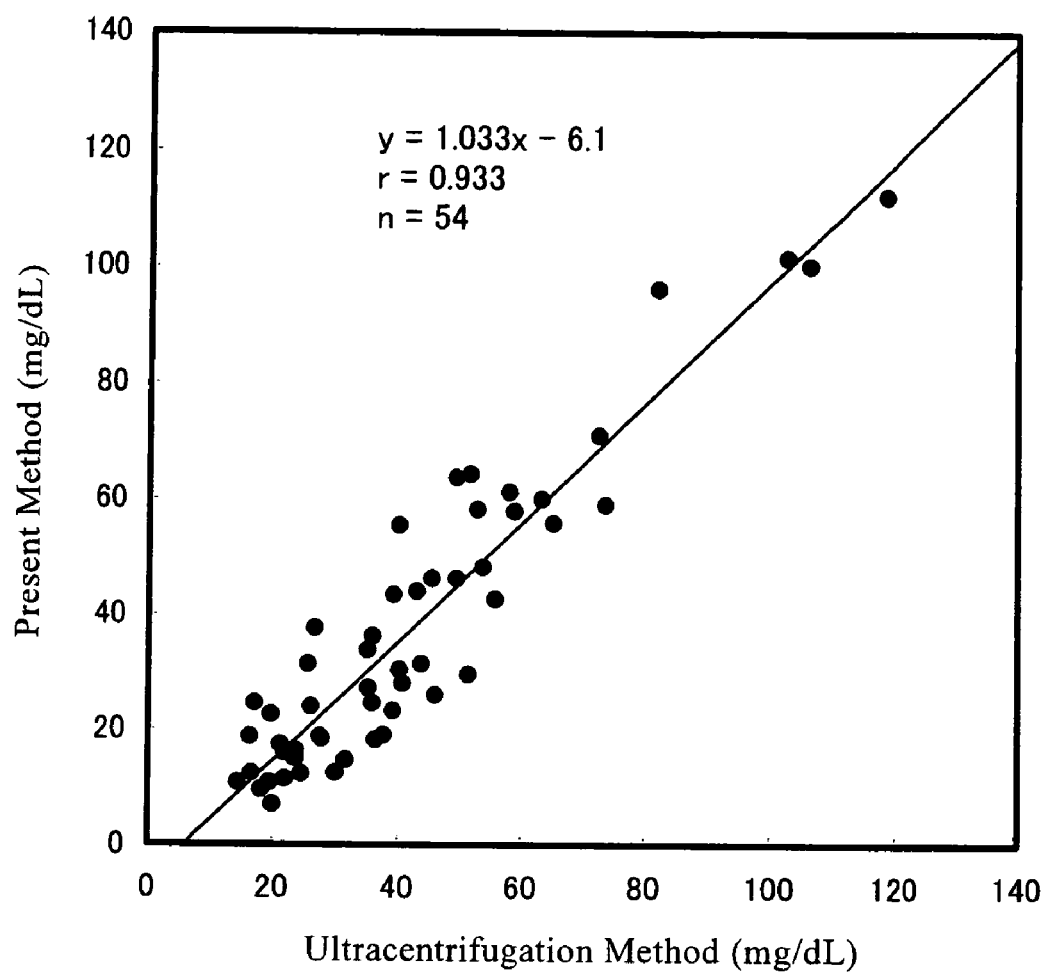
FIG. 3 demonstrates the relationship between the measured value of cholesterol in a small particle LDL according to the method of the present invention in Example 2 and the measured value of cholesterol in a small particle LDL by the ultracentrifugation method.

A small particle LDL in serum sample was measured according to the method of the present invention and the measured values were compared with those obtained by the ultracentrifugation method. The results are shown in FIG. 3.

One hundred μl of the test sample was mixed with 100 μl of the separation solution containing 300 U/mL of sodium heparin and 150 mmol/L $MgCl_2$ and allowed to react at 37° C. for 10 min. After the reaction, the mixture was centrifuged at 18,500 g for 15 mins, and the supernatant was recovered and analyzed for cholesterol in the small particle LDL by a commercial kit LDL-EX(N) (DENKA SEIKEN Co) using Autoanalyzer, Hitachi 7170. In the ultracentrifugation method, the mixture of the test serum and a density solution was centrifuged to recover the fraction with the density 1.040-1.063. Cholesterol was measured in the recovered fraction to obtain the cholesterol value in the small particle LDL. As shown in FIG. 3, the result of the present invention demonstrated a good co-relation with the result of the ultracentrifugation method.

EXAMPLE 3

Figure 4:
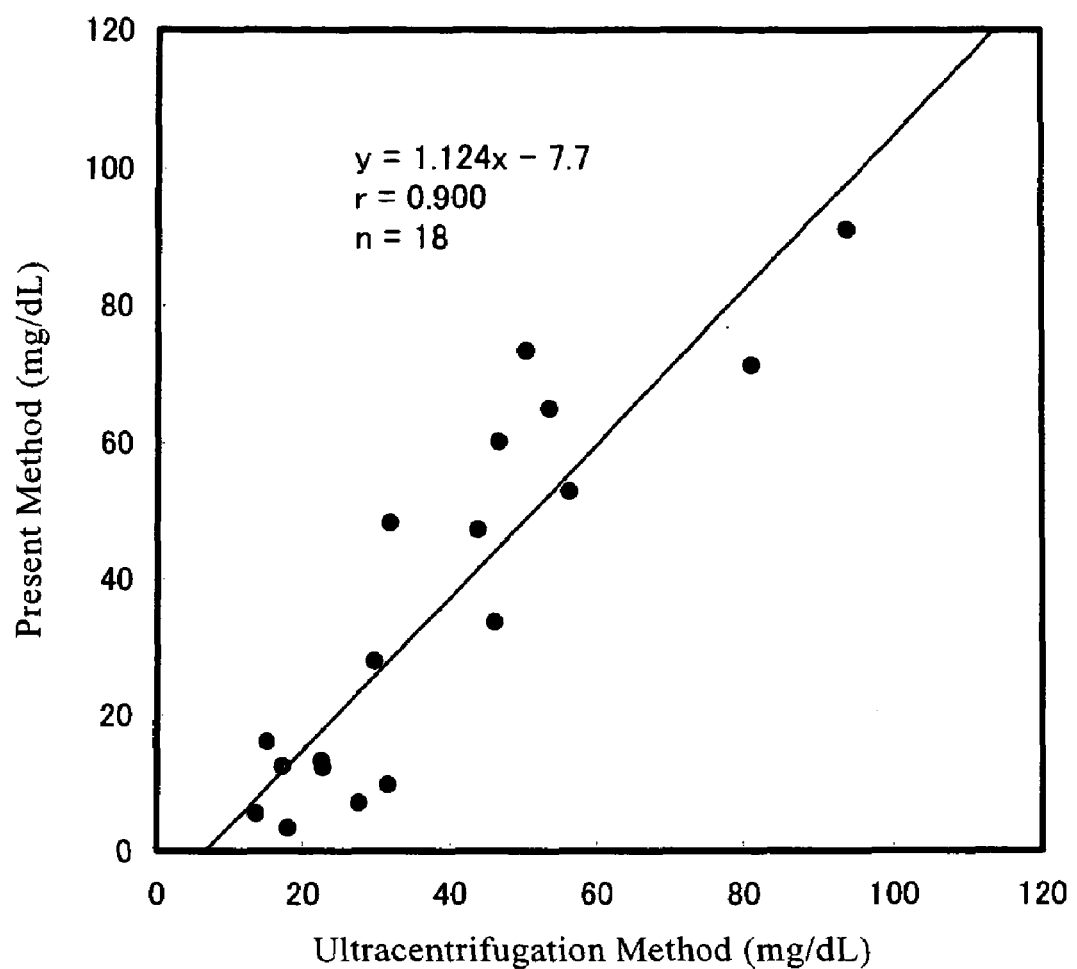
FIG. 4 demonstrates the relationship between the measured value of apoB protein in a small particle LDL according to the method of the present invention in Example 3 and the measured value of apoB protein in a small particle LDL by the ultracentrifugation method.

One hundred μl of a serum test sample was mixed with 100 μl of the separation solution containing 1.5% dextran sulfate with an average molecular weight of 5000 and 40 mmol/L of $MgCl_2$ and allowed to react at 25° C. for 10 mins. After the reaction, the mixture was centrifuged at 18,500 g for 15 mins, the supernatant was recovered and the amount of apoB in a small particle LDL is measured by turbidimetric immuno assay (Daiichi Pure Chemicals Co., ApoB aouto-N(Daiichi)) using anti-human apoB antibody. In the ultracentrifugation method, the mixture of the test serum and the density solution was centrifuged to recover the fraction with the density 1.040-1.063. ApoB was measured to obtain an apoB value in small particle LDL. The result is shown in FIG. 4. As shown in the FIG. 4, the result of the present invention demonstrated a good co-relation with the result of the ultracentrifugation method as was the case with Example 2.

EXAMPLE 4

Figure 5:
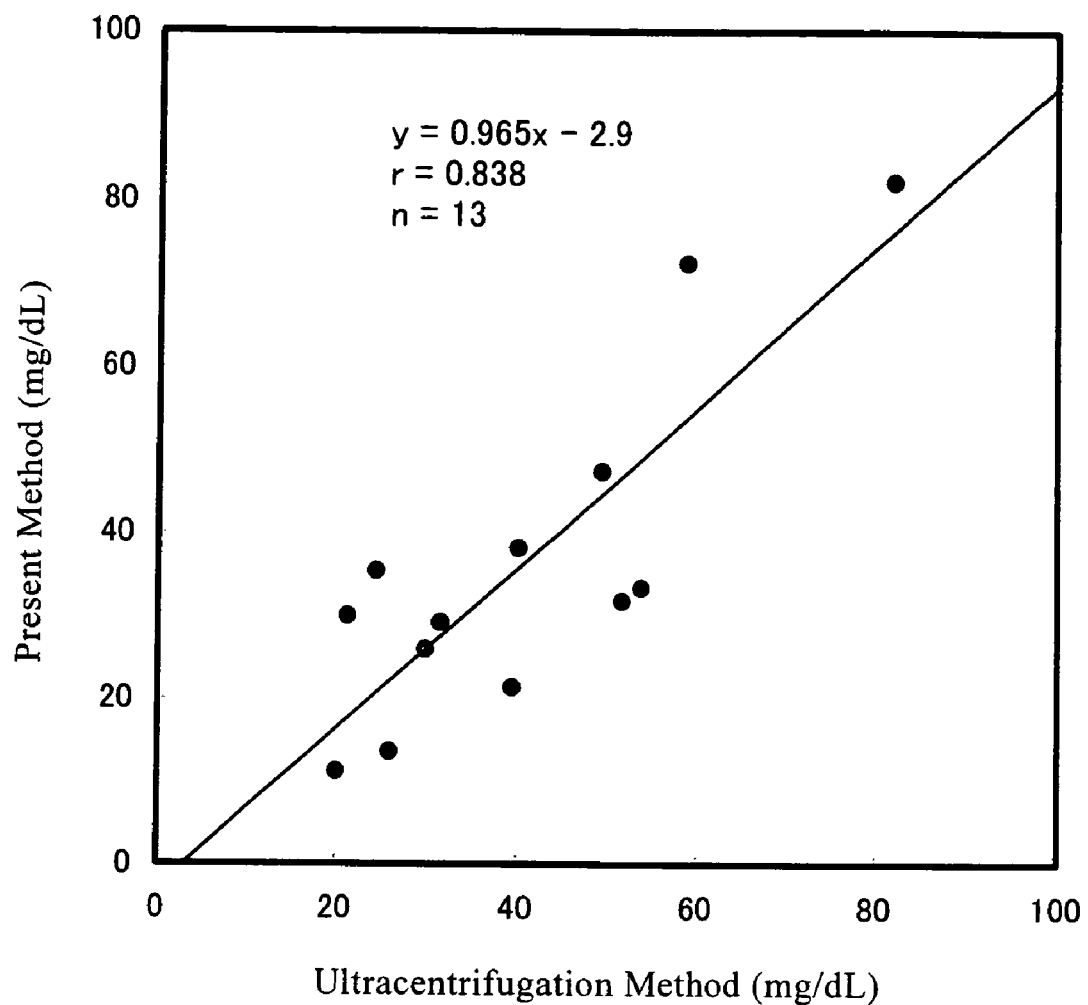
FIG. 5 demonstrates the relationship between the measured value of cholesterol in a small particle LDL according to the method of the present invention in Example 4 and the measured value of cholesterol in a small particle LDL by the ultracentrifugation method.

All the operations were carried out according to Example 2 using the similar reagents except that the separation solution was replaced with 0.3% sodium phosphotungstic acid and 7.5 mmol/L $CaCl_2$, and the measured values according to the present invention were compared with those obtained by the ultracentrifugation method. The result is shown in FIG. 5. As shown in FIG. 5, the result of the present invention demonstrated a good co-relation with the result of the ultracentrifugation method as was the case with Example 2.

EXAMPLE 5

Figure 6:
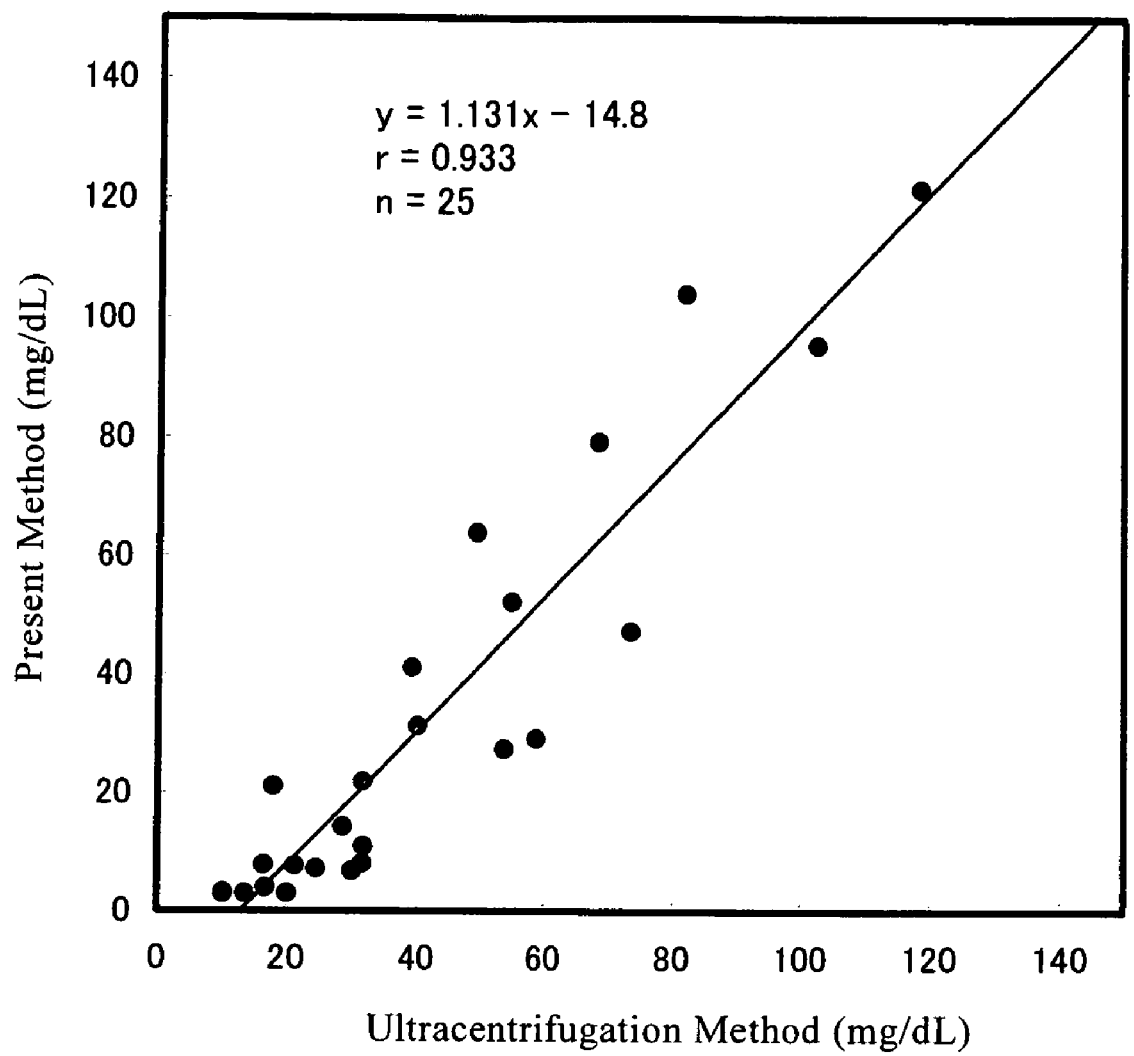
FIG. 6 demonstrates the relationship between the measured value of cholesterol in a small particle LDL according to the method of the present invention in Example 5 and the measured value of cholesterol in a small particle LDL by the ultracentrifugation method.

All the operations were carried out according to Example 2 using the similar reagents except that the separation solution was replaced with 40 U/mL sodium heparin and 30 mmol/L $MnCl_2$, and the measured values according to the present invention were compared with those obtained by the ultracentrifugation method. The result is shown in FIG. 6. As shown in FIG. 6, the result of the present invention demonstrated a good co-relation with the result of the ultracentrifugation method as was the case with the second Example 2.

EXAMPLE 6

Figure 7:
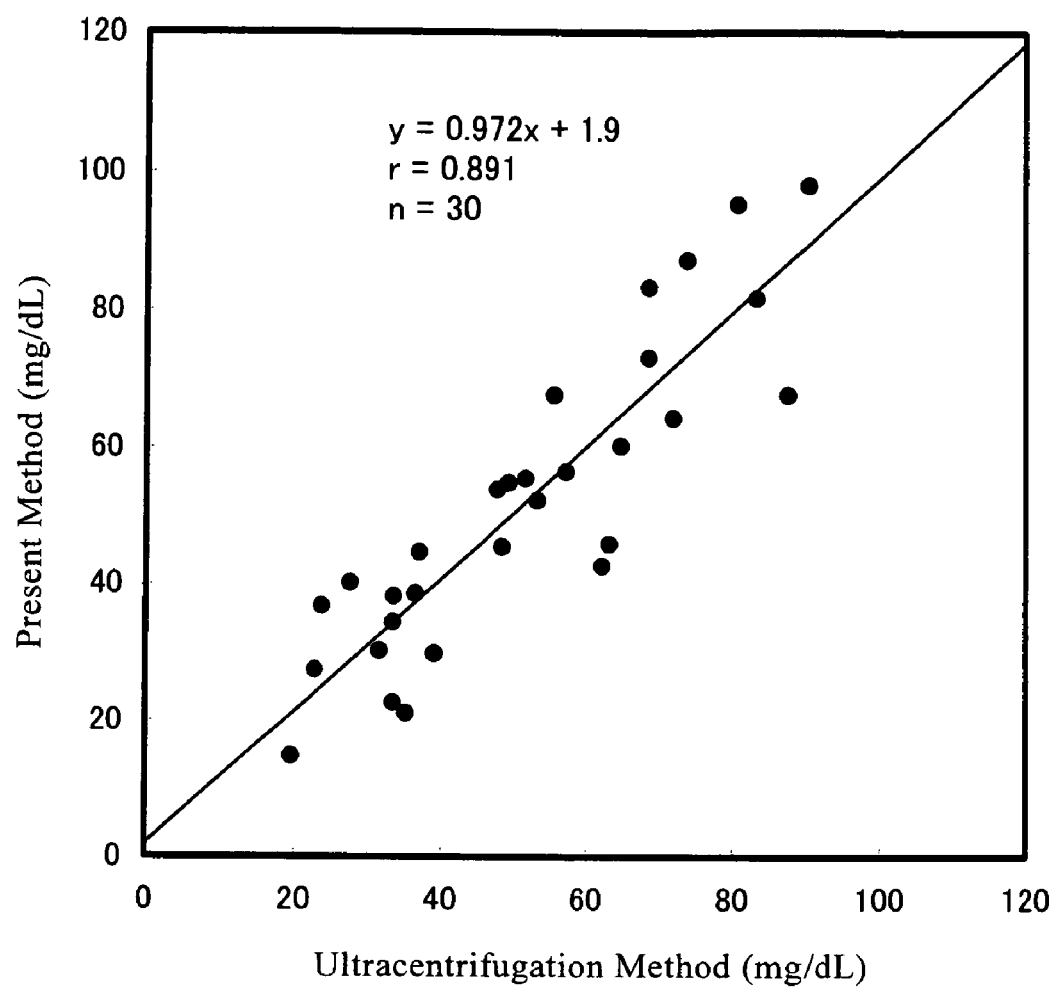
FIG. 7 demonstrates the relationship between the measured value of cholesterol in a small particle LDL according to the method of the present invention in Example 6 and the measured value of cholesterol in a small particle LDL by the ultracentrifugation method.

All the operations were carried out according to Example 2 using the similar reagents except that the separation solution was replaced with 500 U/mL sodium heparin, 140 mmol/L $MgCl_2$ and 34 mmol/L KCl, and the measured values according to the present invention were compared with those obtained by the ultracentrifugation method. The result is shown in FIG. 7. As shown in FIG. 7, the result of the present invention demonstrated a good co-relation with the result of the ultracentrifugation method as was the case with Example 2.

EXAMPLE 7

Figure 8:
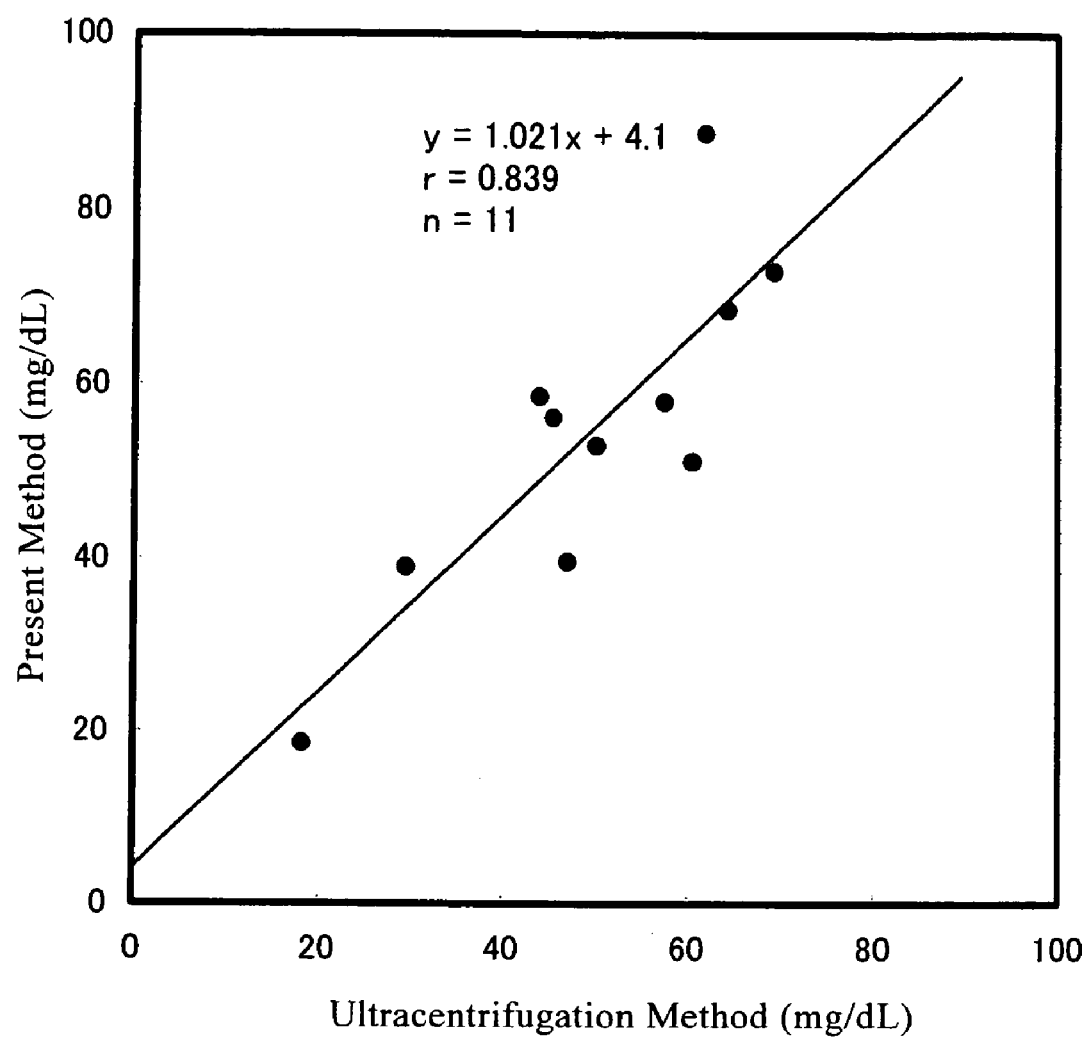
FIG. 8 demonstrates the relationship between the measured value of cholesterol in a small particle LDL according to the method of the present invention in Example 7 and the measured value of cholesterol in a small particle LDL by the ultracentrifugation method.

All the operations were carried out according to Example 2 using the similar reagents except that the separation solution was replaced with 8% PEG (molecular weight: 6,000), and the measured values according to the present invention were compared with those obtained by the ultracentrifugation method. The result is shown in FIG. 8. As shown in FIG. 8, the result of the present invention demonstrated a good co-relation with the result of the ultracentrifugation method as was the case with Example 2.

EXAMPLE 8

Figure 9:
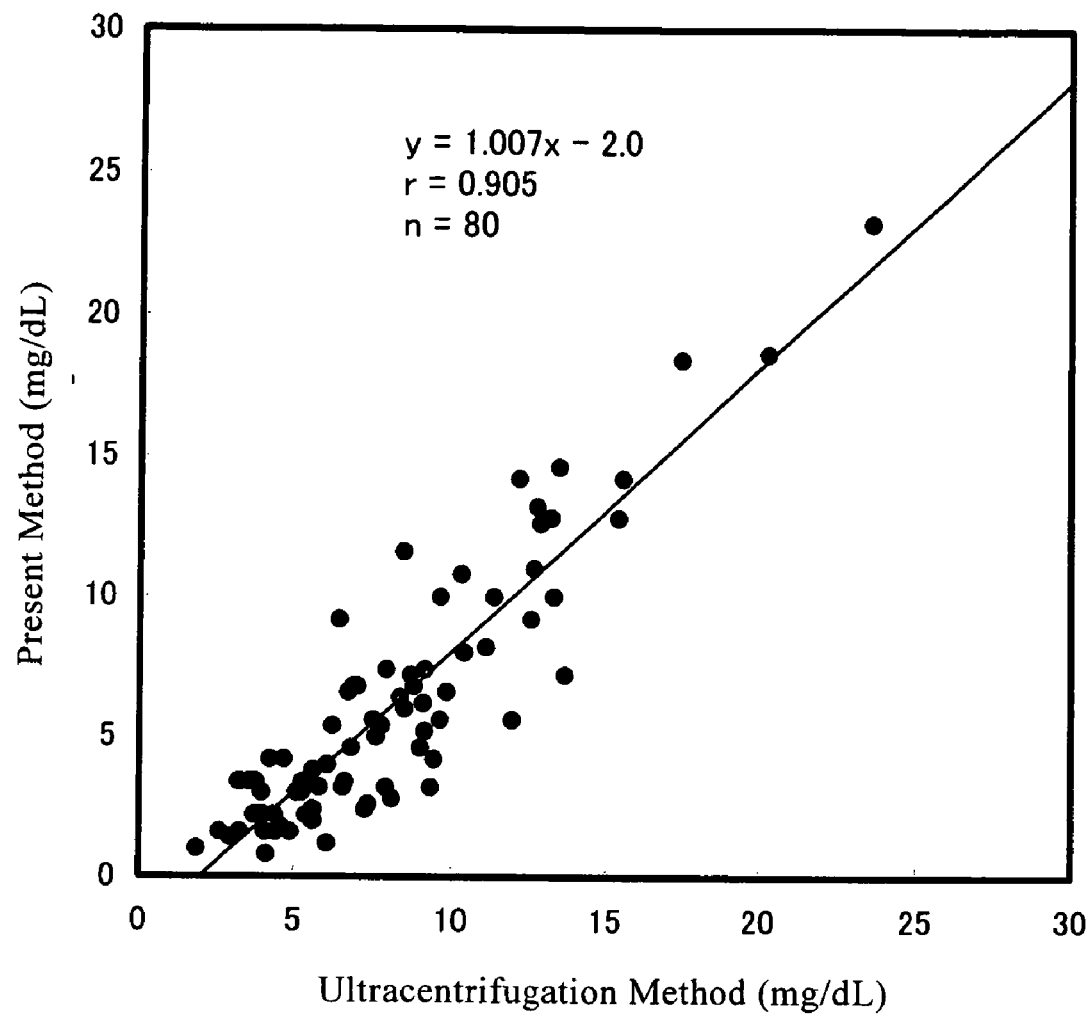
FIG. 9 demonstrates the relationship between the measured value of triglycerides in a small particle LDL according to the method of the present invention in Example 8 and the measured value of triglycerides in a small particle LDL by the ultracentrifugation method.

One hundred μl of a serum test sample was mixed with 100 μl of the separation solution containing 150 U/mL sodium heparin 90 mmol/L of $MgCl_2$ and allowed to react at 37° C. for 10 mins. After the reaction, the mixture was centrifuged at 18,500 g for 15 mins, the supernatant was recovered and the amount of triglycerides in a small particle LDL was measured using a reagent for measuring triglycerides in LDL. In the ultracentrifugation method, the mixture of the test serum and a density solution was centrifuged to recover the fraction with the density 1.040-1.063. Triglycerides were measured in the recovered fraction to obtain the triglyceride value in a small particle LDL. The result is shown in FIG. 9. As shown in FIG. 9, the result of the present invention demonstrated a good co-relation with the result of the ultracentrifugation method as was the case with Example 2.

EXAMPLE 9

Figure 10:
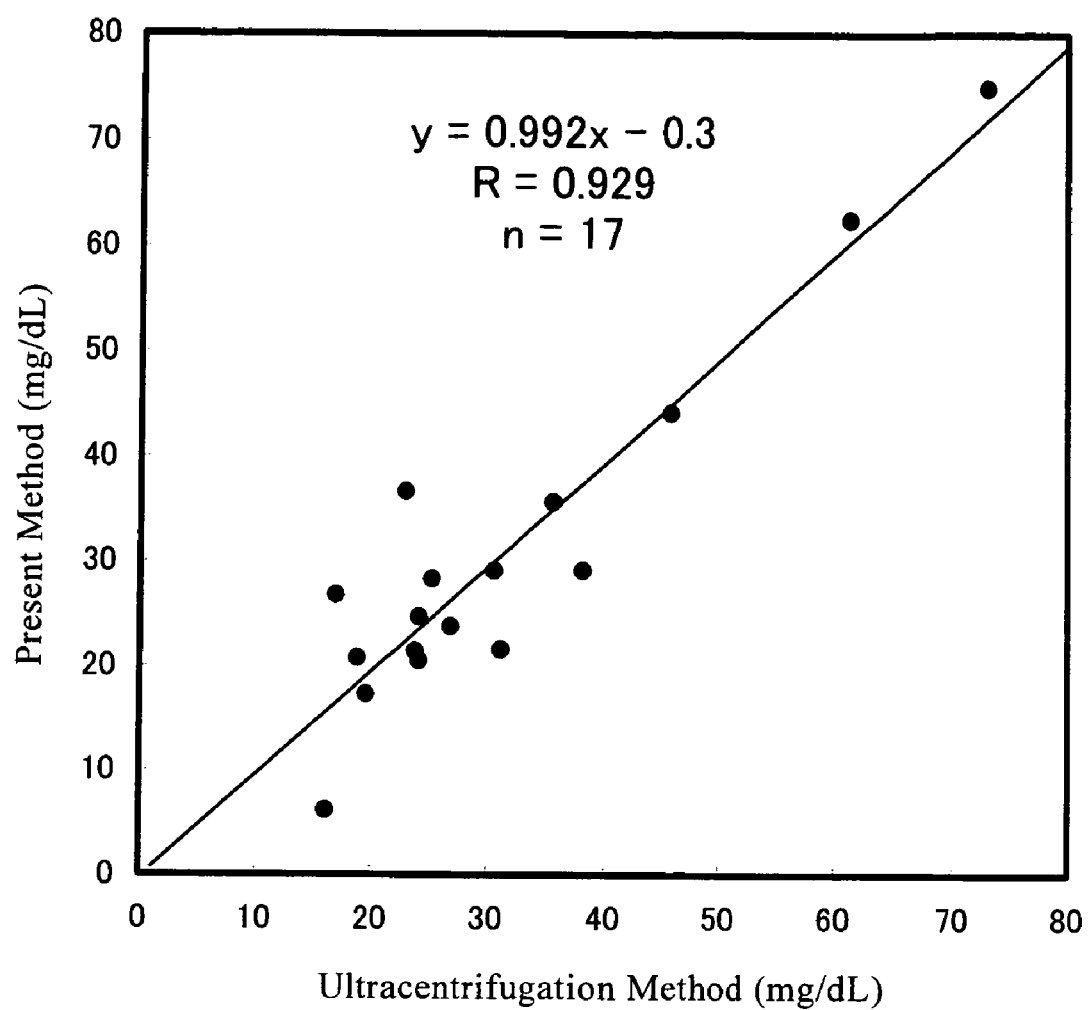
FIG. 10 demonstrates the relationship between the measured value of cholesterol in a small particle LDL according to the method of the present invention in Example 9 and the measured value of cholesterol in a small particle LDL by the ultracentrifugation method.

One hundred μl of a serum test sample was mixed with 100 μl of the separation solution containing 150 U/mL sodium heparin and 90 mmol/L of $MgCl_2$ and allowed to react at 37° C. for 10 mins. After the reaction, the mixture was centrifuged at 10,000 g for 1 min using a centrifugal filter (Ultrafree-MC (0.1 μm Filter Unit) MILLIPORE Co). After recovering the filtrate, cholesterol in a small particle LDL was measured and compared with the cholesterol measurement value obtained by the ultracentrifugation method. The result is shown in FIG. 10. As shown in FIG. 10, the result of the present invention demonstrated a good co-relation with the result of the ultracentrifugation method as was the case with Example 2.

This specification hereby incorporates all the publications, patents and patent applications cited in this specification in their entirety by reference.

Industrial Applicability

According to the present invention, a small particle LDL can be separated with simple procedures from other LDLs, and cholesterol, triglycerides or apoB in a small particle LDL can be fractionally measured. Therefore it is very useful for clinical applications.

The invention claimed is:

1. A method for quantifying small particle LDL in a test sample, comprising:
   (i) removing lipoproteins other than small particle LDL and HDL from said test sample by adding a separation agent comprising a polyanion, a divalent cation, and a monovalent cation, wherein the monovalent cation is at a final concentration of 50 mmol/L or less; then
   (ii) eliminating HDL by treating the test sample with cholesterol esterase and cholesterol oxidase in the presence of a surface active agent that is polyalkylene oxide; and
   (iii) quantifying small particle LDL in the test sample from step (ii) by measuring the amount of LDL.

2. A method according to claim 1, wherein the polyanion is selected from the group consisting of heparin, phosphotungstic acid and dextran sulfate.

3. A method according to claim 2, wherein, when the polyanion is added to the test sample, the final concentration of the polyanion is 10-250 U/mL for heparin, 0.02-1.25% for dextran sulfate and 0.02-1.25% for phosphotungstic acid.

4. A method according to claim 1, wherein the divalent cation is selected from the group consisting of $Mn^{2+}$, $Mg^{2+}$ and $Ca^{2+}$.

5. A method according to claim 4, wherein, when the divalent cation is added to the test sample, the final concentration of the divalent cation is 2.5-35 mmol/L for $Mn^{2+}$, 2.5-125 mmol/L for $Mg^{2+}$ and 1-75 mmol/L for $Ca^{2+}$.

6. A method according to claim 1, wherein the monovalent cation is selected from the group consisting of Na$^+$, K$^+$ and Li$^+$.

7. A method according to claim 1, wherein measuring the amount of LDL is carried out by using a reagent which is used for selectively measuring cholesterol in LDL and which does not require fractionation.

8. A method according to claim 1, wherein measuring the amount of LDL is carried out by using a reagent which is used for selectively measuring triglycerides in LDL and which does not require fractionation.

9. A method according to claim 1, wherein measuring the amount of LDL is carried out by using an anti-human apoprotein B antibody.

10. A method according to claim 1, wherein the surface active agent is selected from the group consisting of polyoxyethylene lauryl ether, polyoxyethylene cetyl ether, polyoxyethylene octylphenyl ether and polyoxyethylene nonylpheny ether.

11. A method for quantifying small particle LDL in a test sample, comprising:
(i) removing lipoproteins other than small particle LDL and HDL from said test sample, by adding a separation agent consisting of polyethylene glycol;
(ii) eliminating HDL by treating the test sample from step (i) with cholesterol esterase and cholesterol oxidase in the presence of a surface active agent, wherein the surface active agent is polyalkylene oxide; and
(iii) quantifying small particle LDL in the test sample from step (ii) by measuring the amount of LDL.

12. A method according to claim 11 wherein the final concentration of polyethylene glycol is 2-5% by weight when polyethylene glycol is added to the test sample.

13. A method according to claim 11, wherein the surface active agent is selected from the group consisting of polyoxyethylene lauryl ether, polyoxyethylene cetyl ether, polyoxyethylene octylphenyl ether and polyoxyethylene nonylpheny ether.

14. A method for separating small particle LDL from a test sample that contains LDLs, comprising precipitating LDLs other than small particle LDL by adding a separation agent comprising a monovalent cation at a final concentration of 50 mmol/L or less to the test sample.

15. A method according to claim 14, wherein said separation agent further comprises a polyanion and a divalent cation.

16. A method according to claim 15, wherein the polyanion is selected from the group consisting of heparin, phosphotungstic acid and dextran sulfate.

17. A method according to claim 16, wherein, when the polyanion is added to the test sample, the final concentration of the polyanion is 10-250 U/mL for heparin, 0.02-1.25% for dextran sulfate and 0.02-1.25% for phosphotungstic acid.

18. A method according to claim 15, wherein the divalent cation is selected from the group consisting of Mn$^{2+}$, Mg$^{2+}$ and Ca$^{2+}$.

19. A method according to claim 18, wherein, when the divalent cation is added to the test sample, the final concentration of the divalent cation is 2.5-35 mmol/L for Mn$^{2+}$, 2.5-125 mmol/L for Mg$^{2+}$ and 1-75 mmol/L for Ca$^{2+}$.

20. A method according to claim 14, wherein the monovalent cation is selected from the group consisting of Na$^+$, K$^+$ and Li$^+$.

* * * * *

UNITED STATES PATENT AND TRADEMARK OFFICE
CERTIFICATE OF CORRECTION

PATENT NO.         : 7,544,515 B2                                     Page 1 of 1
APPLICATION NO. : 10/537766
DATED                 : June 9, 2009
INVENTOR(S)        : Yasuki Itoh and Tsutomu Hirano It is certified that error appears in the above-identified patent and that said Letters Patent is hereby corrected as shown below:

On the title page item (75) should read: Yasuki Itoh, Niigata (JP); ~~Tsutomi~~ Tsutomu Hirano, Tokyo (JP)

Signed and Sealed this

First Day of September, 2009

David J. Kappos
*Director of the United States Patent and Trademark Office*